United States Patent
Awad et al.

(10) Patent No.: US 11,472,044 B2
(45) Date of Patent: Oct. 18, 2022

(54) BINARY PASSIVE VARIABLE STIFFNESS JOINT

(71) Applicant: Khalifa University of Science and Technology, Abu Dhabi (AE)

(72) Inventors: Mohammad Awad, Abu Dhabi (AE); Dongming Gan, Abu Dhabi (AE); Jorge Dias, Abu Dhabi (AE); Lakmal Seneviratne, Abu Dhabi (AE)

(73) Assignee: KHALIFA UNIVERSITY OF SCIENCE AND TECHNOLOGY, Abu Dhabi (AE)

( * ) Notice: Subject to any disclaimer, the term of this patent is extended or adjusted under 35 U.S.C. 154(b) by 339 days.

(21) Appl. No.: 16/643,259

(22) PCT Filed: Aug. 26, 2018

(86) PCT No.: PCT/IB2018/056470
§ 371 (c)(1),
(2) Date: Feb. 28, 2020

(87) PCT Pub. No.: WO2019/043545
PCT Pub. Date: Mar. 7, 2019

(65) Prior Publication Data
US 2020/0254634 A1 Aug. 13, 2020

Related U.S. Application Data

(60) Provisional application No. 62/551,965, filed on Aug. 30, 2017.

(51) Int. Cl.
*B25J 19/06* (2006.01)
*B25J 17/02* (2006.01)
(Continued)

(52) U.S. Cl.
CPC ......... *B25J 19/068* (2013.01); *B25J 17/0208* (2013.01); *F16D 3/10* (2013.01);
(Continued)

(58) Field of Classification Search
CPC ................ B25J 19/068; B25J 17/0208; F16H 2035/006; F16H 35/08
See application file for complete search history.

(56) References Cited

U.S. PATENT DOCUMENTS

| | | | |
|---|---|---|---|
| 9,091,306 B2* | 7/2015 | Orita | B25J 19/068 |
| 11,192,266 B2* | 12/2021 | Schimmels | F16F 1/22 |
| 2020/0326780 A1* | 10/2020 | Kearney | G06F 3/011 |

FOREIGN PATENT DOCUMENTS

| | | | |
|---|---|---|---|
| CN | 204487594 U | | 7/2015 |
| CN | 106863348 A | | 6/2017 |
| CN | 109846672 A | * | 6/2019 |

* cited by examiner

*Primary Examiner* — Sherry L Estremsky
(74) *Attorney, Agent, or Firm* — Hayes Soloway PC

(57) ABSTRACT

A variable stiffness joint and method to alter the stiffness of the joint with multiple stiffness levels is described wherein a plurality of stiffness bits (m) are used for enabling 2 m stiffness level variations for the joint. Each stiffness bit comprises an elastic element in mechanical connection with a clutch (21, 22, 23). The joint revolves with zero stiffness level when all the clutches (21, 22, 23) are disengaged whereas a clutch (21, 22, 23) involves one of the elastic elements which alter the stiffness of the joint. Engaging other clutches (21, 22, 23) involve more elastic elements for altering the joint stiffness and the resultant joint stiffness is determined by adding the stiffness values of all the involved springs (6, 7, 8).

18 Claims, 6 Drawing Sheets

(51) Int. Cl.
  *F16D 3/10*   (2006.01)
  *F16D 3/66*   (2006.01)
  *F16D 3/64*   (2006.01)
  A61B 34/30    (2016.01)
  B25J 9/10     (2006.01)
  B25J 9/12     (2006.01)
  F16D 3/50     (2006.01)
  F16H 57/08    (2006.01)
  F16D 3/56     (2006.01)
(52) U.S. Cl.
  CPC ................ *F16D 3/64* (2013.01); *F16D 3/66* (2013.01); A61B 34/30 (2016.02); B25J 9/102 (2013.01); B25J 9/126 (2013.01); B25J 17/0266 (2013.01); F16D 3/50 (2013.01); F16D 3/56 (2013.01); F16H 57/08 (2013.01)

BINARY PASSIVE VARIABLE STIFFNESS JOINT

CROSS-REFERENCE TO RELATED APPLICATIONS AND PRIORITY

This patent application claims priority from PCT Patent Application No. PCT/IB2018/056470 filed Aug. 26, 2018, which claims priority from U.S. Patent Application No. 62/551,965 filed Aug. 30, 2017. Each of these patent applications are herein incorporated by reference in its/their entirety.

FIELD OF THE INVENTION

The present invention relates to stiffness joints and more specifically, the present invention relates to a variable stiffness joint and method for altering the stiffness of a robotic joint. A stiffness of the joint is varied according to a number of stiffness levels in order to enhance safety interactions.

BACKGROUND OF THE INVENTION

There has been a rapid development in the fields of wearable robotics and compliant actuators during the past few decades. This has resulted in robots operating closely with humans, physically interacting or even being worn by humans which has further led to the rise of several safety aspects and design requirements. Safety should be an essential feature in robots especially in the case of unexpected interactions or sensor failures. Other than the safety aspect, applications such as rehabilitation robots, exoskeletons and haptics have proved that the interaction between the robot and the operator must show adaptability and force accuracy.

Safety and actuation performance initiated the development of variable impedance actuators (VIA), where the actuator mechanical properties like inertia, damping or stiffness affect the system's equilibrium position. This changes the interaction forces to adapt to different situations between robots and the environment or users aiming to provide safer operations and energy efficiency. Then, based on how the impedance (stiffness and damping) is achieved, active and passive variable impedance actuator (VIA) concepts were proposed. In the active-by-control impedance, the behavior of a highly-reduced stiff actuator is altered via software. This concept allowed to adapt both stiffness and damping in a wide range for several speeds. The disadvantages of this system include high energy consumption, the need of accurate and expensive force or torque sensors, complexity of the control system, incapability of storing energy and absorbing shocks. In order to overcome these drawbacks, passive compliant elements were added to the actuator, resulting in the Serial Elastic Actuator (SEA). Drawbacks involved with the SEA included non-optimal performance energy efficiency. An optimal performance required careful tuning of the joint stiffness values. This motivated lots of study and new designs of variable stiffness mechanisms with passive compliance.

Another method used to vary the joint stiffness included changing the spring preload, where stiffness altering was achieved by changing the energy stored in the spring. An evolution of this concept is the antagonistic variable stiffness actuators, where the joint stiffness is varied through the combination of two antagonistic SEAs controlled by two separate motors. Other techniques were applied and several solutions were presented such as using a non-linear connector between the output link and the spring element to adjust the preload of the linear spring, applying a lever mechanism between the output link and the elastic element, or by altering the link length between the pivot and the elastic element or the output link.

Although different variable stiffness joints have been developed they have not been successfully applied to robotic arms due to complex stiffness tuning mechanisms, bulky size and non-ideal stiffness curves.

Variable stiffness actuators have been used in many applications, such as rehabilitation exoskeletons, surgical robotics and multiple haptics applications. Although applying compliant mechanisms to haptic devices has shown several advantages in reducing wear and weight, the disadvantages includes an increased control complexity. The resultant force obtained by altering a compliant element can be the key for force feedback in haptic devices.

Generally, all the previous designs involve a continuous stiffness tuning curve from low to high or zero to infinity with a motor based control. Accordingly, there exists a need to provide a mechanism to alter the stiffness of a revolute joint for a wide range of stiffness.

SUMMARY OF THE INVENTION

Therefore it is an object of the present invention to provide a system and method for altering the stiffness levels of a robotic joint, which overcomes at least a part of the above disadvantages.

The present invention involves a variable stiffness joint comprising a plurality of stiffness bits (m) for enabling $2^m$ stiffness level variations for the variable stiffness joint, wherein each stiffness bit comprises an elastic element in mechanical connection with a clutch.

In an embodiment, the elastic elements are torsional springs.

In another embodiment, the clutches are electromagnetic friction clutches.

In another embodiment, the torsional springs are connected to the clutches, which are grounded.

In another embodiment, the torsional springs are Hook's type torsional springs or Linear torsional springs.

In another embodiment, each of the torsional springs is encapsulated in a spring holder.

In an embodiment of the present invention, the variable stiffness joint comprises a lower base and an upper base, wherein the lower base and the upper base are connected using frame rods; a main shaft between the lower and upper base; an output link at the upper base connected to the main shaft for receiving a torque from a user and a gear train comprising a main driving gear connected to the main shaft.

In another embodiment, for each stiffness bit, a planetary gear is in mechanical connection with the main driving gear for engaging the elastic elements using the torque for activating the clutch.

In another embodiment of the present invention, the elastic elements are torsional springs.

In another embodiment of the present invention, the clutches are electromagnetic friction clutches.

In another embodiment of the present invention, the torsional springs are Hook's type torsional springs or Linear torsional springs, connected to the clutches which are grounded.

In another embodiment of the present invention, each of the torsional springs is encapsulated in a spring holder.

In another embodiment of the present invention, each one of the spring holders comprise an upper container and a lower container and each one of the upper containers are mounted on shafts which hold first and second torque reduction stages.

In another embodiment of the present invention, the first torque reduction stage connects the upper container of the spring holder through a (1:5) torque reduction ratio, and the second torque reduction stage with a (1:5) torque reduction ratio, transmits torque to the clutches resulting in a (1:10) torque reduction.

Considering another aspect of the present invention, a method for altering a stiffness level of a robotic or revolute joint is proposed, wherein the method comprises providing an output link for enabling a user to create a torque; using the torque for rotating a main shaft with a main driving gear; and transmitting the torque from the main shaft into a plurality of elastic elements using planetary gears.

In an embodiment, the torque from the plurality of elastic elements is transmitted to activate grounded clutches for altering the stiffness level of the joint, wherein the stiffness is at zero level if the clutches are disengaged or inactive.

In another embodiment of the present invention, the torque is transmitted into the plurality of elastic elements through planetary gears associated with a sun gear, wherein lower ends of the plurality of elastic elements are connected to the planetary gears.

In another embodiment of the present invention, the torque is transmitted from the plurality of elastic elements to grounded clutches through torque reduction stages.

In another embodiment of the present invention, a first torque reduction stage connects to upper ends of the plurality of elastic elements and the torque is transmitted from the plurality of elastic elements to grounded clutches through a second torque reduction stage.

In another embodiment of the present invention, a number of series—parallel elastic elements (m) are involved to achieve $2^m$ levels of stiffness.

In another embodiment of the present invention, an elastic element in mechanical connection with a clutch forms a stiffness bit and each stiffness bit contributes torque on the output link if the clutch associated with the respective stiffness bit is active.

In a preferable embodiment of the present invention, a variable stiffness joint with variable stiffness levels is disclosed, comprising an output link for enabling a user to create a torque; stiffness bits, wherein each stiffness bit comprises an elastic element in mechanical connection with a clutch; and a mechanical mechanism to transfer the torque to the stiffness bits, wherein a selection on the levels of stiffness are made based on the torque.

In another embodiment of the present invention, m number of stiffness bits is used to achieve $2^m$ levels of stiffness.

In another embodiment, the elastic element is a torsional spring.

In another embodiment, the clutch is an electromagnetic friction clutch.

In another embodiment, the torsional spring is connected to the clutch which is grounded.

In another embodiment, the torsional spring is a Hook's type torsional spring or a Linear torsional spring.

In another embodiment, the mechanical mechanism includes two torque reduction stages.

In another embodiment, a first torque reduction stage connects to an upper end of the elastic element and a second torque reduction stage transmits the torque to the clutch.

In another embodiment of the present invention, variable joint stiffness is achieved if the clutch to which the torque is transferred, is engaged or active.

In another embodiment of the present invention, zero joint stiffness is achieved if the clutch to which the torque is transferred is disengaged or inactive.

In another embodiment of the present invention, a transparent mode involves disengaging the clutches and enabling free rotation of the joint.

In another embodiment of the present invention, a variable stiffness mode is activated when the elastic elements are selectively grounded via the clutches.

BRIEF DESCRIPTION OF THE DRAWINGS

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings in which:

DETAILED DESCRIPTION OF THE INVENTION

Figure 1:
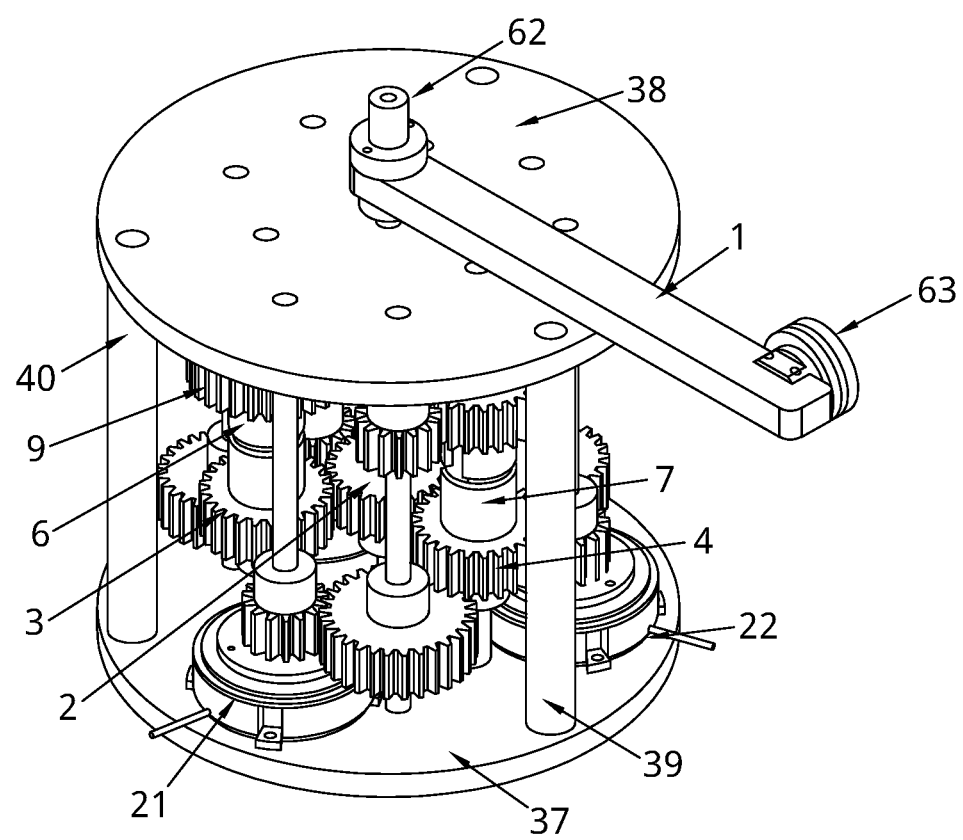
FIG. 1 shows an oblique view of the passive binary controlled variable stiffness joint (BpVSJ) in accordance with an embodiment of the present invention.
Figure 2:
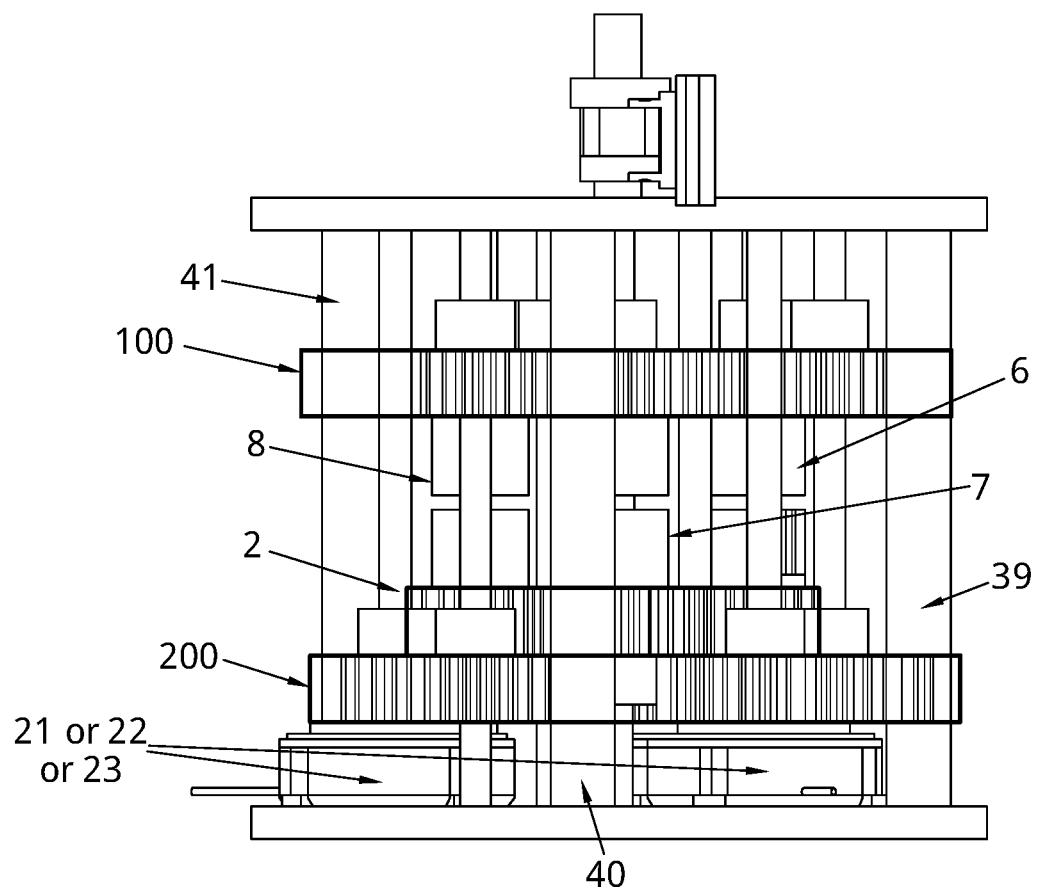
FIG. 2 illustrates gear trains and actuators (clutches) of the passive binary controlled variable stiffness joint (BpVSJ) in accordance with an embodiment of the present invention.
Figure 3:
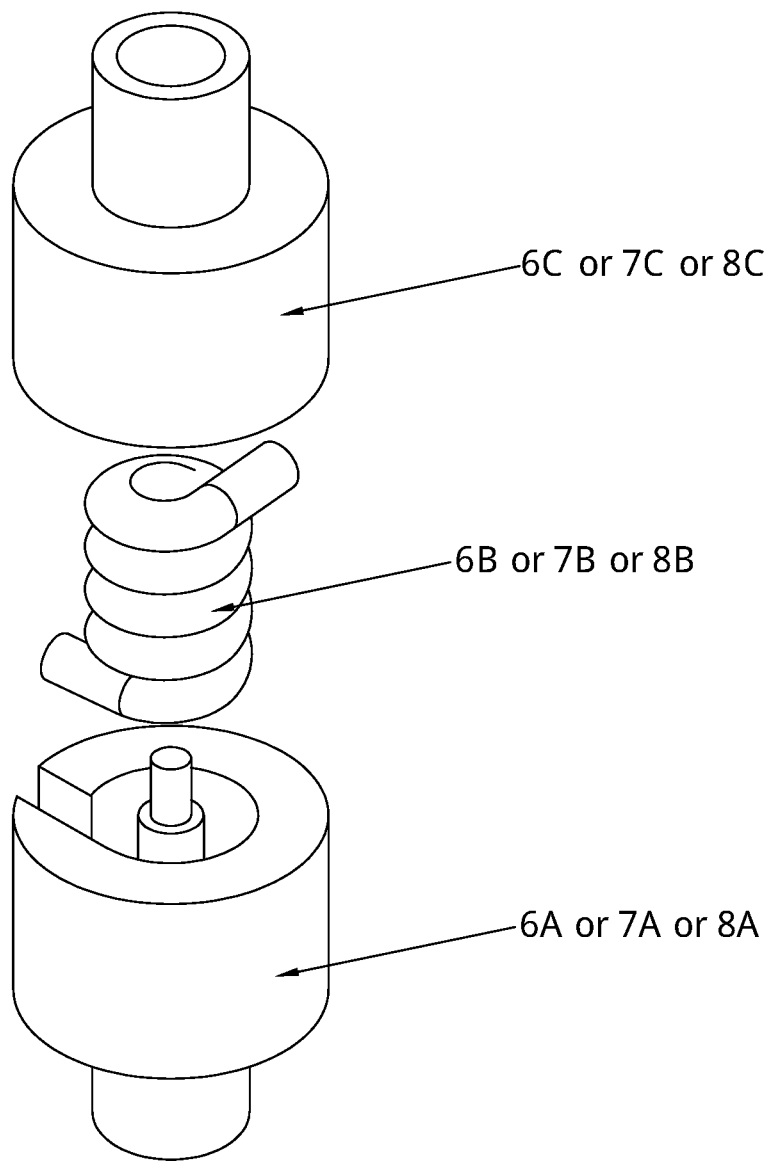
FIG. 3 shows an exploded assembly of the spring compartment and torsional spring used in the passive binary controlled variable stiffness joint (BpVSJ) in accordance with an embodiment of the present invention.

The invention introduces a system and mechanism to alter the stiffness of a robotic revolute joint according to a number of stiffness levels, by proposing the design of a passive binary controlled variable stiffness joint (BpVSJ).

In a preferred embodiment of the invention, as shown in FIG. 1-6, the structure of the variable stiffness joint comprises of two bases 37 and 38 connected using three frame rods 39, 40, and 41. An output link 1 is mounted on a shaft 24 which is mounted on bases 37 and 38. Shaft 24 holds also a main driving gear 2 which connects with three planetary gears 3, 4, and 5 in a (1:1) ratio. Each of these three gears is mounted on shafts 25, 26 and 27 respectively. These shafts are held to the lower base 37. Each of these shafts holds the lower container—6A, 7A and 8A respectively—of three elastic elements 6B, 7B and 8B respectively. The elastic elements are torsional springs. Each of these torsional springs is encapsulated in upper containers 6C, 7C and 8C respectively, which are mounted on shafts 28, 29 and 30 respectively. These shafts are mounted on base 38.

In an embodiment, the three torsional springs used as elastic elements for the variable stiffness joint structure, are Hook's type torsional springs.

In an embodiment, the three torsional springs used as elastic elements for the variable stiffness joint structure, are linear torsional springs.

Each of the three torsional springs 6B, 7B and 8B are connected to three grounded clutches 21, 22 and 23 respectively. Each set of spring—clutch connection represents a Stiffness Bit in a binary representation of stiffness levels.

In an embodiment of the invention, the three grounded clutches 21, 22 and 23 used in combination with the three torsional springs 6B, 7B and 8B are electromagnetic friction clutches.

The structure of the variable stiffness joint further includes two stages of torque reduction gear trains. The shafts 28, 29 and 30 hold a first torque reduction stage 100. The first torque reduction stage 100 involves two sets of gears. Shafts 28, 29 and 30 hold a first set of gears 9, 10 and 11 for the first torque reduction gear train. Gears 9, 10 and 11 are connected to a second set of gears 12, 13 and 14 respectively to complete the first torque reduction stage 100 of the two stage torque reduction gear train. Gears 12, 13 and 14 are mounted on shafts 31, 32 and 33 respectively and each of these shafts is mounted on bases 37 and 38.

Each of the shafts 31, 32 and 33 hold a first set of gears 15, 16 and 17 of the second torque reduction stage 200 of the two stage torque reduction gear train. Gears 15, 16 and 17 are connected to a second set of gears 18, 19 and 20 respectively to complete the second torque reduction stage 200 of the two stage torque reduction gear train. Gears 18, 19 and 20 are mounted on shafts 34, 35 and 36 respectively and each of these shafts is mounted on bases 37 and 38.

Figure 4:
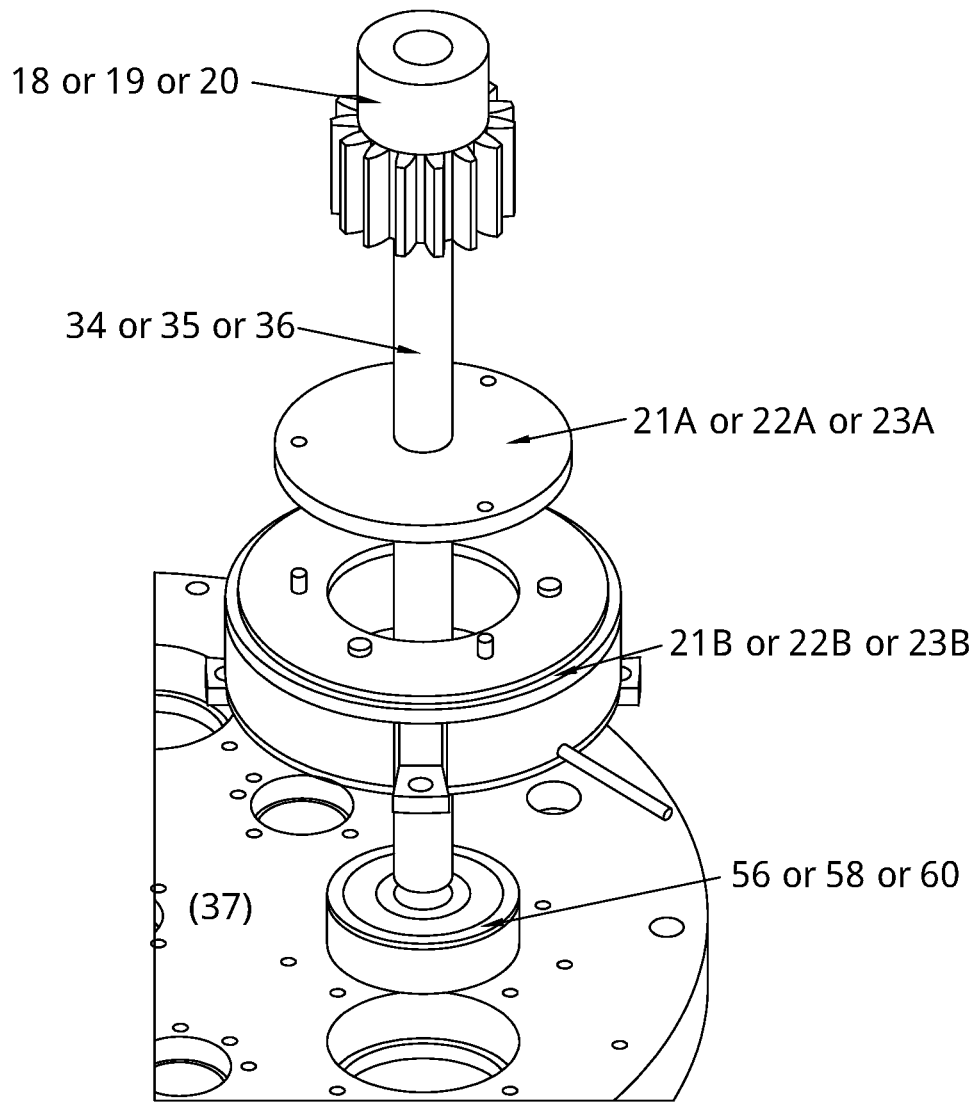
FIG. 4 shows an exploded assembly of the lower part of a clutch shaft used in the passive binary controlled variable stiffness joint (BpVSJ) in accordance with an embodiment of the present invention.

Additionally, the shafts 31, 32 and 33 hold dynamic parts 21A, 22A, and 23A respectively, of the three grounded clutches 21, 22, and 23, as shown in FIG. 4. Stationary parts of the grounded clutches 21B, 22B and 23B are mounted on base 37.

The first torque reduction gear train 100 connects the upper containers 6C, 7C and 8C of the torsional spring encapsulations through a (1:5) torque reduction ratio. The second stage of torque reduction 200 further includes a (1:5) torque reduction ratio. This second stage of torque reduction 200 transmits torque to the grounded clutches 21, 22 and 23, resulting in a total ratio of (1:10) torque reduction.

In an embodiment of the present invention, the mechanical system designed to implement a passive binary—controlled variable stiffness joint (BpVSJ) includes a fixed lower base 37. The lower base 37 consists of ten bearings that hold ten shafts. Three of these shafts are connected to the three electromagnetic friction clutches 21, 22 and 23, which are grounded. Four shafts are used for a sun—planetary gear train, wherein the planetary gears 3, 4 and 5, hold the three torsional springs 6, 7 and 8. The last three shafts are used for the two torque reduction stages since the selected grounded clutches may not be able to hold the designated torque.

In a further embodiment of the invention, a sensory system may be enabled using a mount 62 for an encoder, and a mount 63 for a force/torque sensor.

In a preferred embodiment of the present invention, a method or mechanism for altering the stiffness levels of a revolute joint involves an output link or arm 1, which is connected on shaft 24. The main driving gear (sun gear) 2 is held by shaft 24 and connects with three planetary gears 3, 4 and 5 in a (1:1) ratio. A torque is transmitted from a user's hand through the output link 1. The output link 1 is connected to the sun gear 2 which transmits the torque to the torsional springs 6, 7 and 8 holders through the planetary gears 3, 4 and 5. The other ends 6A, 7A and 8A of each spring is connected to the planetary gears 3, 4 and 5 which contribute part of the resultant torque on the sun gear 2. The first torque reduction stage 100 involving gears 9, 10, 11, 12, 13 and 14, connects the upper containers of the torsional spring encapsulations 6C, 7C and 8C through a (1:5) torque reduction ratio. The second stage of torque reduction 200 including a (1:5) torque reduction ratio involving gears 15, 16, 17, 18, 19 and 20, transmits this torque to the three grounded clutches 21, 22 and 23, resulting in a total (1:10) torque reduction.

Figure 5:
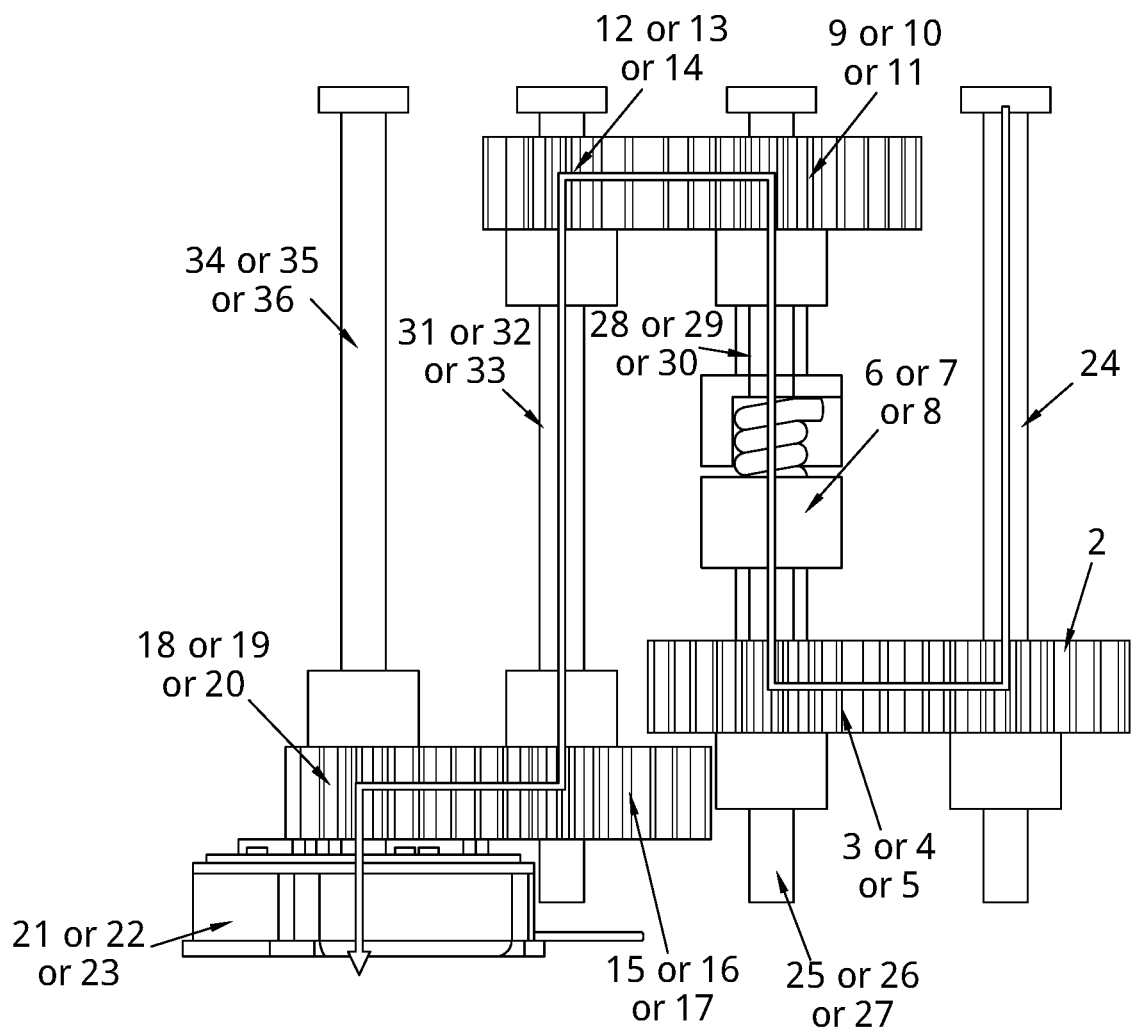
FIG. 5 describes torque transmission path through one of the bit stages involved in the passive binary controlled variable stiffness joint (BpVSJ) in accordance with an embodiment of the present invention.

In a further embodiment, the proposed variable stiffness mechanism functions in two modes. The first mode involves a scenario where the stiffness is to be minimized which allows a user to deflect the output arm 1, with an unlimited range of deflection. This mode is the transparent mode. The output link possesses zero stiffness with infinite angle deflection unless a change in the joint stiffness is required. The three springs 6, 7 and 8 may rotate freely with the output link using lower shafts 25, 26, and 27 and upper shafts 28, 29 and 30. As shown in FIG. 5, the torque or motion during the transparent mode travels through a path from output link 1 through the main gear 2, to the planetary gears 3, 4, and 5. The torque then passes through the torsional spring compartments 6, 7 and 8, to the first torque reduction gear train, the second torque reduction gear train and then to the grounded bearings.

The other mode is required when a significant change in stiffness is needed. This second mode, the variable stiffness mode, is activated when a significant value of stiffness is required. This desired value may be either one or the sum of the stiffness values of the two or three elastic elements or springs. The values of the torsional spring's constants follow a binary sequence as shown below:

$$k_n = 2^{n-1}(k_0), n \in \{1,2,3\} \quad (1)$$

where $k_0$ is the base stiffness value (which may be selected by a designer). The value of n represents the number of spring stages. The values of ($k_0$, n) provide design flexibility with respect to compactness, desired levels of stiffness, and range of stiffness.

The springs 6, 7 and 8 can be selectively grounded through clutches 21, 22 and 23 respectively. When a clutch is active or engaged, torque flows from output link 1 through the main gear 2, to the planetary gears 3, 4, and 5. The torque then passes through the torsional spring compartments 6, 7 and 8, to the first torque reduction gear train, the second torque reduction gear train and then to the grounded bearings.

The equation for determining the joint stiffness is as follows:

$$K_\theta = \Sigma_{i=1}^{m} b_i 2^{i-1}(k_0) \quad (1)$$

$b_i = \{0,$ if clutch (i) is inactive; 1, if clutch (i) is active
where m is the number of spring-clutch stages. The levels of stiffness may be represented in binary form and are shown in the form of a table. The table displays seven levels of stiffness obtained from 3 Stiffness Bits for k0=0.5 Nm/degree.

| $b_3$ | $b_2$ | $b_1$ | Stiffness level | Stiffness (N · m/degree) | Torque (N · m) @ 10 degrees |
|---|---|---|---|---|---|
| 0 | 0 | 0 | 0 | 0 | 0 |
| 0 | 0 | 1 | $K_0$ | 0.5 | 5 |
| 0 | 1 | 0 | 2 $K_0$ | 1.0 | 10 |
| 0 | 1 | 1 | 3 $K_0$ | 1.5 | 15 |
| 1 | 0 | 0 | 4 $K_0$ | 2.0 | 20 |
| 1 | 0 | 1 | 5 $K_0$ | 2.5 | 25 |
| 1 | 1 | 0 | 6 $K_0$ | 3.0 | 30 |
| 1 | 1 | 1 | 7 $K_0$ | 3.5 | 35 |

Each of the three torsional springs 6, 7 and 8 are connected to three grounded clutches 21, 22 and 23 respectively. Each set of spring—clutch connection represents a Stiffness Bit in a binary representation of stiffness levels. In accordance with the proposed variable stiffness mechanism, if one of the grounded clutches is active or engaged, the output arm 1 deflects the corresponding spring which leads to the user feeling an altered stiffness. This mode is called a variable stiffness mode. A Stiffness Bit contributes torque on the output arm 1, if the bit's clutch is active.

However, if the grounded clutches are inactive or disengaged, the gears will rotate freely and the user will feel no stiffness. This will facilitate the capability of unlimited motion of the output arm 1, at zero stiffness level where all clutches are inactive, resulting in a transparent mode.

In an embodiment, the levels of stiffness may be represented in binary form. An active Stiffness Bit is represented by '1' and an inactive Stiffness Bit is represented by '0'. This feature of the present invention provides a capability of altering the stiffness levels instantaneously at any joint deflection position, with low level switching time of 4 ms.

In another embodiment of the invention, the three torsional springs 6, 7 and 8, have three different stiffness values ($K_0$, $2K_0$, $4K_0$) respectively, and are connected to the three grounded-clutches 21, 22 and 23. Hence, scalability of the variable stiffness mechanism may be achieved either by changing the value of the seed stiffness value $K_0$, or by adding extra stiffness bits.

Considering another embodiment, the passive binary controlled variable stiffness joint (BpVSJ) may be designed as a passive haptic interface capable to simulate different level stiffness in virtual reality and remote environment applications. Assuming that the desired maximum output torque is 35 N·m @ 10 degrees and there are three Stiffness Bits to simulate seven levels of stiffness, the springs should have stiffness levels of 0.5 N·m/degree, 1 N·m/degree, and 2 N·m/degree for the first, second and third Stiffness Bits, respectively.

Figure 6:
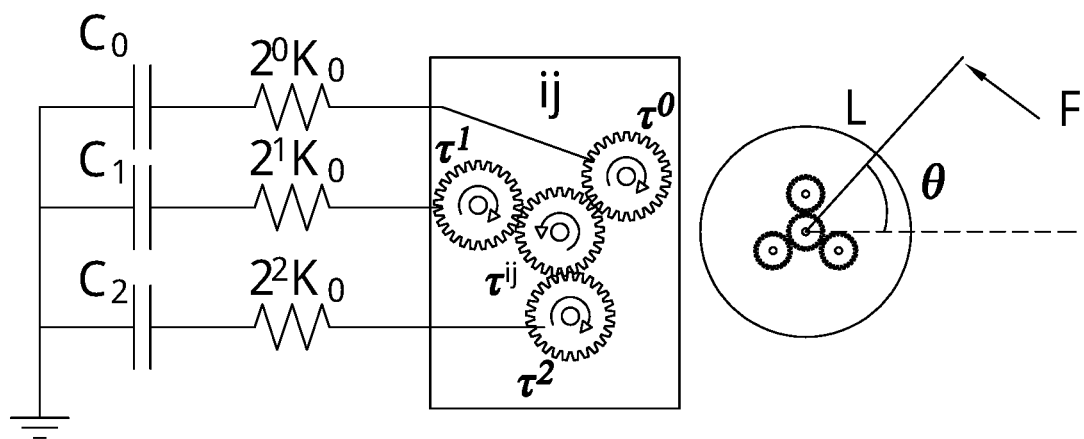
FIG. 6 illustrates the stiffness model associated with an embodiment of the present invention.

Altering the stiffness of the variable stiffness joint, BpVSJ is achieved by changing the number of parallel elastic elements involved in the system. The involvement of an elastic element is achieved through grounding one end of the torsional spring (elastic element) via an electromagnetic clutch. The stiffness model may be derived from a kinematics model of the joint as shown in FIG. 6.

The stiffness model may be derived starting with the resultant torque represented as $\tau^{\in}$. The equation is as follows:

$$\tau^{\in} = F \times L = -(\tau^0 + \tau^1 + \tau^2) \quad (2)$$

wherein $\tau 0$, $\tau 1$ and $\tau 2$ are the torque values corresponding to the stiffness bits 0, 1 and 2 respectively.

F is a pushing force exerted by a user's hand which creates a torque through the arm length, L. The resultant torque $\tau^{\in}$ will rotate the main shaft 24 with the sun gear 2. In the case where all the Stiffness Bits are inactive, the torque is transmitted freely through the planetary gears 3, 4 and 5, into the torsional springs 6, 7 and 8 which will rotate freely. However in the case of any active Stiffness Bits, motion of a shaft connecting the end of the involved torsional spring to the clutch will be blocked. Hence when torque is exerted on the main shaft, the torsional springs that are involved will produce a counter torque that is felt as resistance force on a user's hand.

Each of these torques can be represented using the following equation:

$$\tau^n = \beta_n(2^n(K_0)(\theta - \phi n - \varphi)), n \in \{0,1,2\} \quad (3)$$

$$\phi n = \theta(t_{ON,n}), n \in \{0,1,2\} \quad (4)$$

$$\beta n = \{0, \text{ if clutch } (n) \text{ is inactive}; 1, \text{ if clutch } (n) \text{ is active} \quad (5)$$

where ($\beta$, $\theta$, $\phi$, $\varphi$) is the binary function, the joint angular position, the joint angular position at the activation time ($t_{ON}$), and the backlash angle, respectively. The joint stiffness is the rate of change of torque with respect to the angular deflection. Considering FIGS. 6, C0, C1 and C2 denote the clutches associated with the first, second and third springs denoted by 20K0, 21K0 and 22K0 respectively.

Considering the previous equations, the stiffness equation be driven as follows:

$$\tau^{\Sigma} = \Sigma_0 \beta_n(2^n(K_0)(\theta - \phi_n - \varphi)), n \in \{0,1,2\} \quad (6)$$

$$K_{\Sigma} = \delta\tau^{\Sigma}/\delta\theta = \Sigma_0^n \beta_n(2^n(K_0)), n \in \{0,1,2\} \quad (7)$$

With consideration to equation number (7), the joint stiffness is dependent on the number of Stiffness Bits (n) and the seed stiffness value ($K_0$). This feature allows for scalability of the model with respect to both the stiffness range and the realized number of stiffness values.

In another embodiment, the actuators of industrial or domestic robots may be replaced with the variable stiffness joint mechanism proposed by the present invention, in order to enhance safer robotic interactions.

Many changes, modifications, variations and other uses and applications of the subject invention will become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. A variable stiffness joint comprising an m number of stiffness bits for enabling $2^m$ stiffness level variations for the variable stiffness joint, wherein each stiffness bit comprises an elastic element in mechanical connection with a clutch.

2. A variable stiffness joint according to claim 1 comprising:
 a lower base and an upper base, wherein the lower base and the upper base are connected using frame rods;
 a main shaft between the lower and upper base;
 an output link at the upper base connected to the main shaft for receiving a torque from a user;
 a gear train comprising a main driving gear connected to the main shaft; and
 for each stiffness bit,
 a planetary gear in mechanical connection with the main driving gear.

3. A variable stiffness joint according to claim 2, wherein the elastic elements are torsional springs.

4. A variable stiffness joint according to claim 3, wherein the torsional springs are Hook's type torsional springs or Linear torsional springs, connected to the clutches which are grounded.

5. A variable stiffness joint according to claim 3, wherein each of the torsional springs is encapsulated in a spring holder.

6. A variable stiffness joint according to claim 5, wherein each one of the spring holders comprise an upper container and a lower container and each one of the upper containers are mounted on shafts which hold first and second torque reduction stages.

7. A variable stiffness joint according to claim 6 wherein,
the first torque reduction stage connects the upper container of the spring holder through a 1:5 torque reduction ratio, and
the second torque reduction stage with a 1:5 torque reduction ratio, transmits torque to the clutches resulting in a 1:10 torque reduction.

8. A variable stiffness joint according to claim 2, wherein the clutches are electromagnetic friction clutches.

9. A method for altering a stiffness level of a robotic or revolute joint, the method comprising:
providing an output link for enabling a user to create a torque;
using the torque for rotating a main shaft with a main driving gear;
transmitting the torque from the main shaft into a plurality of elastic elements using planetary gears;
transmitting the torque for altering the stiffness level of the joint,
wherein the stiffness is at zero level if a plurality of clutches are disengaged or inactive.

10. The method according to claim 9, wherein the torque is transmitted into the plurality of elastic elements through planetary gears associated with a sun gear, wherein lower ends of the plurality of elastic elements are connected to the planetary gears.

11. The method according to claim 9, wherein the torque is transmitted from the plurality of elastic elements to grounded clutches through torque reduction stages.

12. The method according to claim 11, wherein a first torque reduction stage connects to upper ends of the plurality of elastic elements and the torque is transmitted from the plurality of elastic elements to grounded clutches through a second torque reduction stage.

13. The method according to claim 9, wherein an m number of series-parallel elastic elements are involved to achieve $2^m$ levels of stiffness.

14. The method according to claim 9, wherein one of the elastic elements from the plurality of elastic elements in mechanical connection with one of the clutches selected from the plurality of clutches forms a stiffness bit and the stiffness bit contributes torque on the output link if the clutch associated with the stiffness bit is active.

15. A variable stiffness joint with variable stiffness levels, comprising:
an output link for enabling a user to create a torque;
stiffness bits, wherein each stiffness bit comprises an elastic element in mechanical connection with a clutch;
a mechanical mechanism to transfer the torque to the stiffness bits, wherein a selection on the levels of stiffness are made based on the torque.

16. The variable stiffness joint according to claim 15, wherein m number of stiffness bits is used to achieve $2^m$ levels of stiffness.

17. The variable stiffness joint according to claim 15, wherein a transparent mode involves disengaging the clutches and enabling free rotation of the joint.

18. The variable stiffness joint according to claim 15, wherein a variable stiffness mode is activated when the elastic elements are selectively grounded via the clutches.

* * * * *